United States Patent
Aikawa et al.

(10) Patent No.: US 8,585,203 B2
(45) Date of Patent: Nov. 19, 2013

(54) OPHTHALMOLOGIC PHOTOGRAPHING APPARATUS

(75) Inventors: Satoshi Aikawa, Yokohama (JP); Hideyuki Ooban, Kawaguchi (JP); Tomoyuki Iwanaga, Yokohama (JP); Toshifumi Masaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 74 days.

(21) Appl. No.: 13/320,248

(22) PCT Filed: May 18, 2010

(86) PCT No.: PCT/JP2010/003325
§ 371 (c)(1),
(2), (4) Date: Nov. 11, 2011

(87) PCT Pub. No.: WO2010/134318
PCT Pub. Date: Nov. 25, 2010

(65) Prior Publication Data
US 2012/0057128 A1 Mar. 8, 2012

(30) Foreign Application Priority Data
May 22, 2009 (JP) .................................. 2009-124348

(51) Int. Cl.
*A61B 3/14* (2006.01)
*A61B 3/10* (2006.01)

(52) U.S. Cl.
USPC ............ 351/206; 351/208; 351/221; 351/205

(58) Field of Classification Search
USPC ................................................. 351/200–246
See application file for complete search history.

(56) References Cited

U.S. PATENT DOCUMENTS

| | | | |
|---|---|---|---|
| 7,270,415 B2 * | 9/2007 | Yamaguchi et al. | 351/221 |
| 8,226,234 B2 * | 7/2012 | Uchida et al. | 351/208 |
| 2002/0036749 A1 | 3/2002 | Isogai | |
| 2006/0126017 A1 | 6/2006 | Mizuochi | |
| 2012/0033181 A1 * | 2/2012 | Koizumi et al. | 351/208 |

FOREIGN PATENT DOCUMENTS

| | | |
|---|---|---|
| EP | 1752084 A2 | 2/2007 |
| JP | 7-100112 A | 4/1995 |
| JP | 10-314120 A | 12/1998 |
| JP | 2000-287934 A | 10/2000 |
| JP | 2003-305009 A | 10/2003 |
| JP | 2008-43570 A | 2/2008 |

* cited by examiner

*Primary Examiner* — Mohammed Hasan
(74) *Attorney, Agent, or Firm* — Canon U.S.A., Inc., IP Division (57) ABSTRACT

When an observation state by an infrared LED 10 is changed to a photographing state by a xenon lamp 3, a movable mirror 16 is pulled upward and an optical path is switched to an image sensor 17 side. A light guide 22a is shifted by an alignment index drive motor 23 so that an incident portion of an alignment index is shifted from a visible LED 22b to direct to an infrared LED 22c. An outgoing portion of the light guide 22a is set at a position where an image is formed on the image sensor 17 by a wavelength of the infrared LED 22c when an operation distance is appropriate. While changing a luminescent color, a position of a luminescent point of the alignment index is changed by switching the LED by the shift of the light guide 22a.

24 Claims, 9 Drawing Sheets

OPHTHALMOLOGIC PHOTOGRAPHING APPARATUS

TECHNICAL FIELD

The present invention relates to an ocular fundus observation apparatus which can change an observation light source between infrared light and visible light to perform observation.

BACKGROUND ART

In recent years, a mydriatic/non-mydriatic combination type fundus camera has been used in an ocular fundus observation apparatus, particularly in a fundus camera, to reduce a burden of a subject as much as possible. The mydriatic/non-mydriatic combination type fundus camera can perform mydriatic photographing and non-mydriatic photographing corresponding to contents of examination by one fundus camera.

Generally, infrared light is used in observation before non-mydriatic photographing, and visible light is used in observation before mydriatic photographing. In Japanese Patent Application Laid-Open No. 7-100112, it is discussed that visible light and infrared light are selectively used as an observation light source of an eye to be examined and a wavelength of an alignment index projection light source is changed corresponding to the observation light source, thereby improving visibility of an alignment index.

In Japanese Patent Application Laid-Open No. 2003-305009, a fundus camera is discussed which selectively uses visible light and infrared light as a light source of observation of an eye to be examined and uses near infrared light as an alignment light source. This fundus camera improves visibility of an alignment index by increasing a quantity of light of the alignment light source in case of visible light observation more than that in case of infrared light observation.

In Japanese Patent Application Laid-Open No. 2000-287934, a position for projecting an alignment index is shifted in a direction of an optical axis in case of photographing a center of an ocular fundus of an eye to be examined and in case of photographing the periphery thereof, thereby suppressing occurrence of flare.

However, as discussed in Japanese Patent Application Laid-Open No. 7-100112, when a wavelength of an alignment index projection light source is changed, a focus is changed with a difference between the wavelengths and an alignment index is deviated there from. Thus, it becomes difficult to obtain correct focus.

Further, a method discussed in Japanese Patent Application Laid-Open No. 2003-305009 in which an alignment index is provided by near infrared light and the luminance thereof is changed corresponding to an observation wavelength, is needed to enhance the intensity of light of less-visible wavelength in visible light observation. Even if this method can be recognized by an examiner, visibility is hardly excellent for a subject.

A method discussed in Japanese Patent Application Laid-Open No. 2000-287934 in which the position for projecting the alignment index is shifted to suppress occurrence of flare is not devised a measure to improve the visibility when the characteristic of the observation light source is changed.

CITATION LIST

Patent Literature

PTL 1: Japanese Patent Application Laid-Open No. 7-100112

PTL 2: Japanese Patent Application Laid-Open No. 2003-305009

PTL 3: Japanese Patent Application Laid-Open No. 2000-287934

SUMMARY OF INVENTION

The present invention is directed to an ocular fundus observation apparatus which can select a color of an alignment index which is excellent in visibility to an observation light source when the observation light source is changed and can obtain a suitable focal state to the selected color.

According to an aspect of the present invention, an ocular fundus observation apparatus includes an illumination optical system configured to illuminate an ocular fundus of an eye to be examined, an observation photographing optical system configured to observe and photograph the ocular fundus illuminated by the illumination optical system, an alignment index unit which is configured to project an alignment index on an anterior eye portion of the eye to be examined in order to adjust a position relation between the observation photographing optical system and the eye to be examined, and is disposed to cause an image of a luminescent spot of the alignment index to be formed when an alignment is aligned with the anterior eye portion by shifting the observation photographing optical system, an infrared index light source configured to emit near infrared light and a visible index light source configured to emit visible light which are provided on the alignment index unit, an index light source change unit configured to change these index light sources, an index projection unit configured to cause the index light source to emit light, and a shift control unit configured to control a position of the index projection unit in a direction of an optical axis, wherein a position of the luminescent spot of the index projection unit is changed by the shift control unit according to selection of the index light source of the index light source change unit.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

Figure 1:
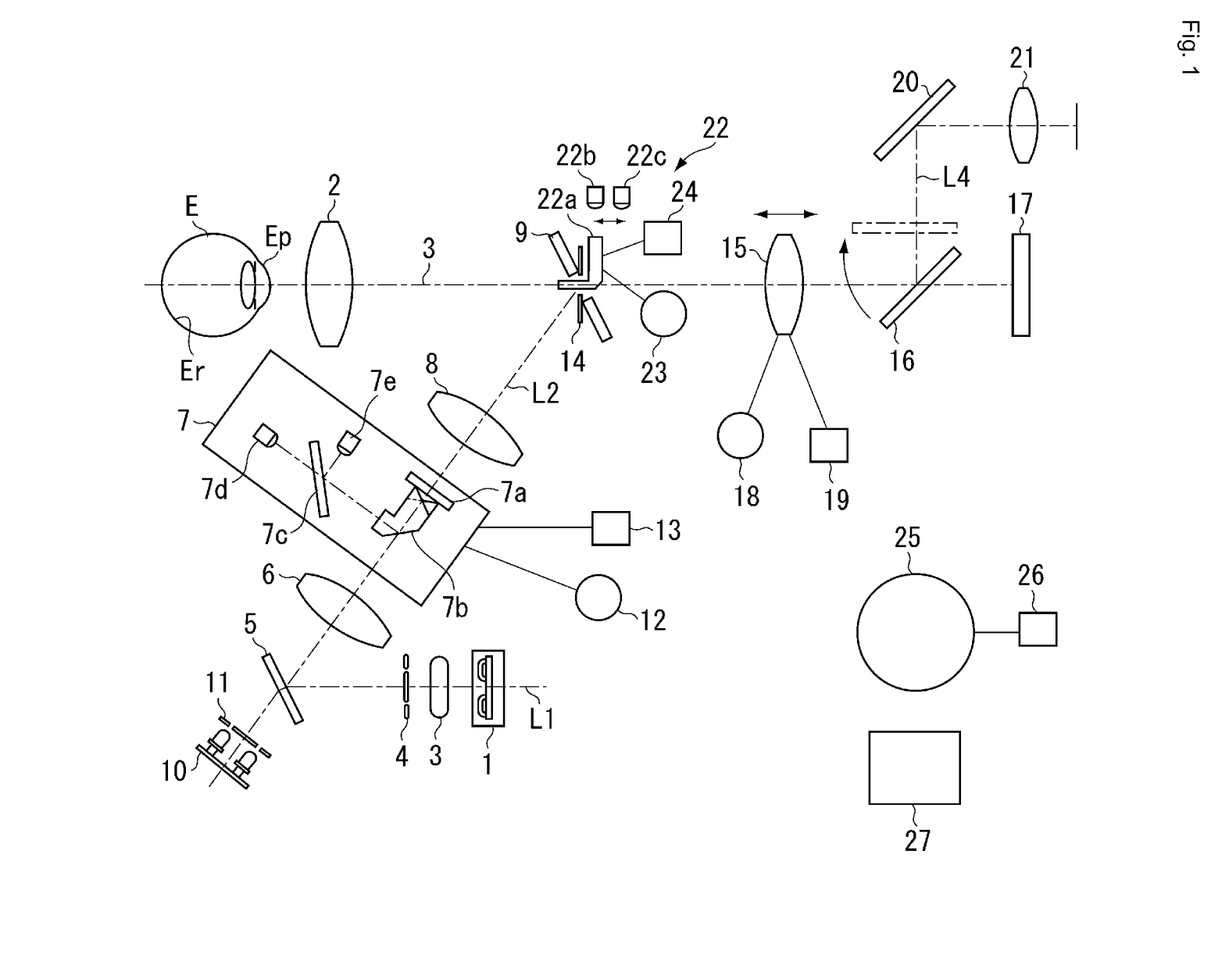
FIG. 1 is a block diagram illustrating a fundus camera according to a first exemplary embodiment.

FIG. 1 is a block diagram illustrating a fundus camera according to a first exemplary embodiment. In an illumination optical system from a halogen lamp 1 to an objective lens 2 disposed in front of an eye to be examined E, the halogen lamp 1 as an observation light source, a xenon lamp 3 as a photographing light source, a visible light ring slit 4, and a dichroic mirror 5 are arranged on an optical path L1. Further, on an optical path L2 on the reflection side of the dichroic mirror 5, a relay lens 6, a prism unit 7, a relay lens 8, and a perforated mirror 9 are arranged. Furthermore, in a direction coaxial with the optical path L2 in the rear of the dichroic mirror 5, an infrared light emitting diode (LED) 10 as an observation light source and an infrared ring slit 11 are provided.

The halogen lamp 1 is a first observation light source of visible light to be used when an ocular fundus Er of the eye to be examined E is observed by visible light. The xenon lamp 3 is the photographing light source to be used when the ocular fundus Er is photographed by visible light. The infrared LED 10 is a second observation light source to be used when the ocular fundus Er is observed by infrared light. The visible light ring slit 4 is a mask for subjecting illumination light from the xenon lamp 3 and the halogen lamp 1 to ring illumination. The infrared ring slit 11 is a mask for subjecting illumination light from the infrared LED 10 to ring illumination. The dichroic mirror 5 has characteristics for reflecting visible light and transmitting infrared light.

The prism unit 7 is provided with a split mask 7a on the optical path L2 and a split prism 7b is attached in the rear of the split mask 7a. A dichroic mirror 7c is disposed in a direction of reflection on the split prism 7b. A visible LED 7d is disposed in a direction of transmission to the dichroic mirror 7c. A near infrared LED 7e is disposed in a direction of reflection on the dichroic mirror 7c. A split drive motor 12 and a split position detection unit 13 are provided on the prism unit 7 to drive the prism unit 7, so that a split image on the ocular fundus Er is shifted and a position thereof can be detected.

On an optical path L3 in the front of the eye to be examined E, the objective lens 2, the perforated mirror 9, a diaphragm 14, a focus lens 15, a movable mirror 16, and an image sensor 17 are arranged in this order. Thus, an observation photographing optical system is configured. On the focus lens 15, a focus lens drive motor 18 and a focus lens position detection unit 19 are attached to drive the focus lens 15, so that the focus lens 15 can come into focus and be detected the position thereof.

On an optical path L4 in a direction of reflection on the movable mirror 16, a fixed mirror 20 and a finder eyepiece lens 21 are arranged. Thus, a visible light observation optical system is configured.

In the hole of the perforated mirror 9, a light guide 22a of an alignment index unit 22 is disposed for adjusting a position relation between the observation photographing optical system and the eye to be examined E. The alignment index unit 22 includes the light guide 22a directed to the eye to be examined E, and a visible LED 22b for emitting visible light and an infrared LED 22c for emitting infrared light which are provided in the vicinity of the incident portion of the light guide 22a. The visible LED 22b and the infrared LED 22c are disposed side by side in a direction of an optical axis. The incident portion of the light guide 22a is directed in a direction orthogonal to the optical axis. Further, for the alignment index unit 22, an alignment index drive motor 23 and an alignment index position detection unit 24 which serve as a shift control unit and an index light source change unit of the alignment index unit 22 are provided.

For the fundus camera, a focus adjustment knob 25, a focus adjustment detection unit 26, and an observation light source selection switch 27 are provided. The observation light source selection switch 27 allows an examiner to alternatively select visible/infrared light from the halogen lamp 1 and the infrared LED When the ocular fundus of the eye to be examined E is observed, visible light emitted from the halogen lamp 1 passes through the xenon lamp 3 and the visible light ring slit 4, and is reflected by the dichroic mirror 5. The visible light reflected by the dichroic mirror 5 passes through the relay lens 6, the prism unit 7, and the relay lens 8, is reflected by the perforated mirror 9, and is incident on the eye to be examined E via the objective lens 2.

When the ocular fundus is observed, infrared light emitted from the infrared LED 10 transmits the infrared ring slit 11 and the dichroic mirror 5, then passes through an optical path similar to the illumination light from the halogen lamp 1, and is incident on the eye to be examined E. At this time, the optical paths of visible light ring illumination light and infrared light ring illumination light are integrated by the dichroic mirror 5, and the ring illumination is subjected to image formation on the ocular fundus Er of the eye to be examined E by the relay lenses 6 and 8.

An ocular fundus image obtained by the illumination is formed at a position of the diaphragm 14 in the vicinity of the perforated mirror 9 by the objective lens 2 and further travels through the observation photographing optical system. The focus lens 15 is shifted in a direction indicated by an arrow in FIG. 1 by an operation of the focus adjustment knob 25, so that focus adjustment to photographing light passing through the perforated mirror 9 is performed. The focus adjustment knob 25 can be operated by the examiner to adjust to a desired focus state and the position thereof is detected by the focus adjustment detection unit 26.

The movable mirror 16 descends in observation by visible light as illustrated in FIG. 1, to introduce the ocular fundus image into the finder eyepiece lens 21 via the fixed mirror 20 on the visible light observation optical system, so that the examiner can observe the ocular fundus image via the finder eyepiece lens 21. The movable mirror 16 ascends during infrared observation and photographing to introduce photographing light into the image sensor 17 on the observation photographing optical system. The image sensor 17 performs photoelectric conversion of the photographing light. An obtained electric signal is subjected to analog-to-digital (A/D) conversion by a processing circuit. The photographed image is displayed by a display unit (not illustrated) during infrared observation and recorded on a recording medium during photographing.

Figure 2A:
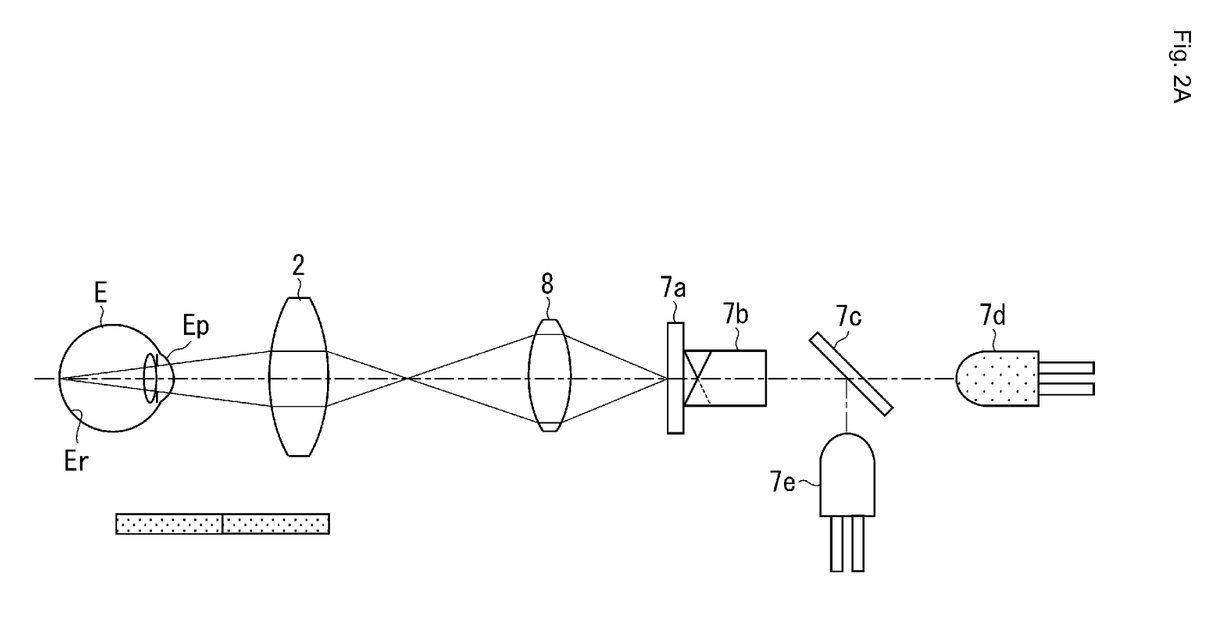
FIG. 2A is a development elevation illustrating a split optical system.
Figure 2B:
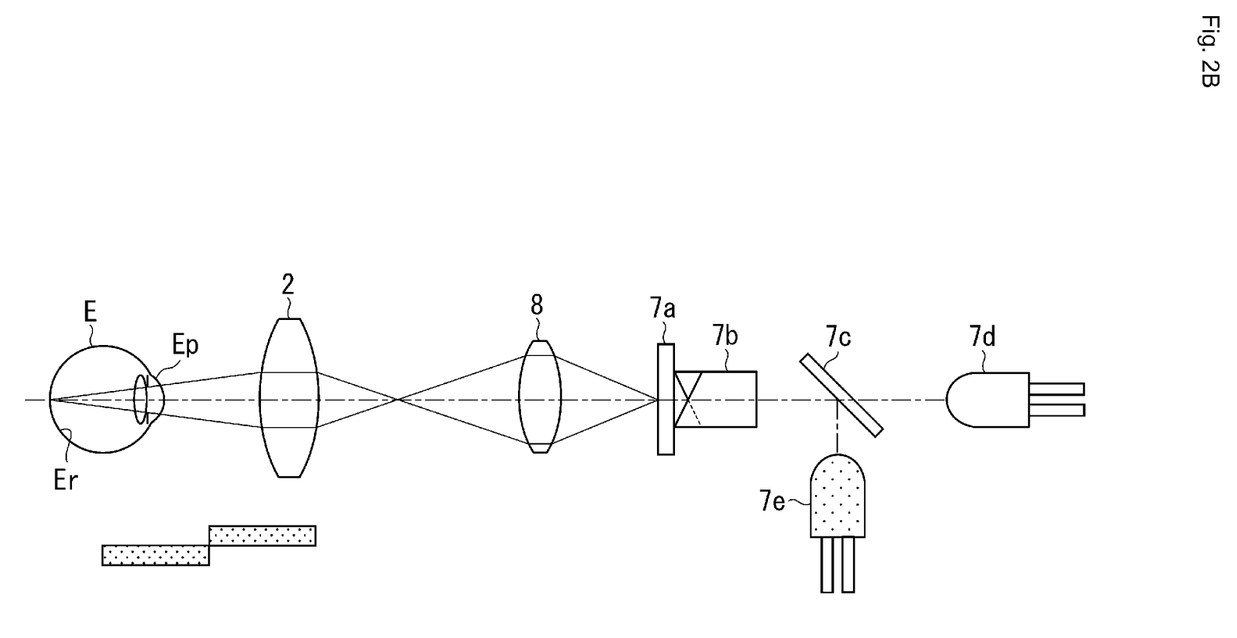
FIG. 2B is a development elevation illustrating a split optical system.

FIGS. 2A and 2B are development elevations illustrating a split optical system according to the first exemplary embodiment. A reflection surface of the split prism 7b and a reflection surface of the perforated mirror 9 are omitted from drawing. The optical system is developed and illustrated. As illustrated in FIG. 2A, a luminous flux when the visible LED 7d is turned on transmits the dichroic mirror 7c and is split by the split prism 7b. A split image results in a straight-line image by the split mask 7a disposed in a close position to the split prism 7b. Accordingly, the image is formed on the perforated mirror 9 by the relay lens 8, and two split images are projected on the ocular fundus Er by the objective lens 2 in a state of a straight line similarly when the split visible LED is emitted.

As illustrated in FIG. 2B, when the visible LED 7d to be turned on in this state is changed to the near infrared LED 7e, a change in optical path length occurs by chromatic aberration due to a difference in color of the LEDs. When the near infrared LED 7e is turned on, a luminous flux thereof is reflected by the dichroic mirror 7c and then travels the similar light path to the visible LED 7d. However, because the optical path length is elongated by the chromatic aberration, the image is formed apart farther than the ocular fundus Er. Thus, as illustrated in FIG. 2B, the two split images cause a deviation between the right and left straight-line images.

Thus, a table is provided so that a stop position of the prism unit 7 in the direction of the optical axis with respect to a stop position of the focus adjustment knob 25 is shifted corresponding to observation light set by the observation light source selection switch 27.

In the alignment index unit 22, the visible LED 22b as a visible index light source emits green light of 530 to 580 nm and has excellent visibility in observation by visible light. The infrared LED 22c as an infrared index light source emits near infrared light to the extent of 700 nm and does not make the eye to be examined E without mydriasis feel glare while retaining visibility, so that miosis can be prevented.

Figure 3:
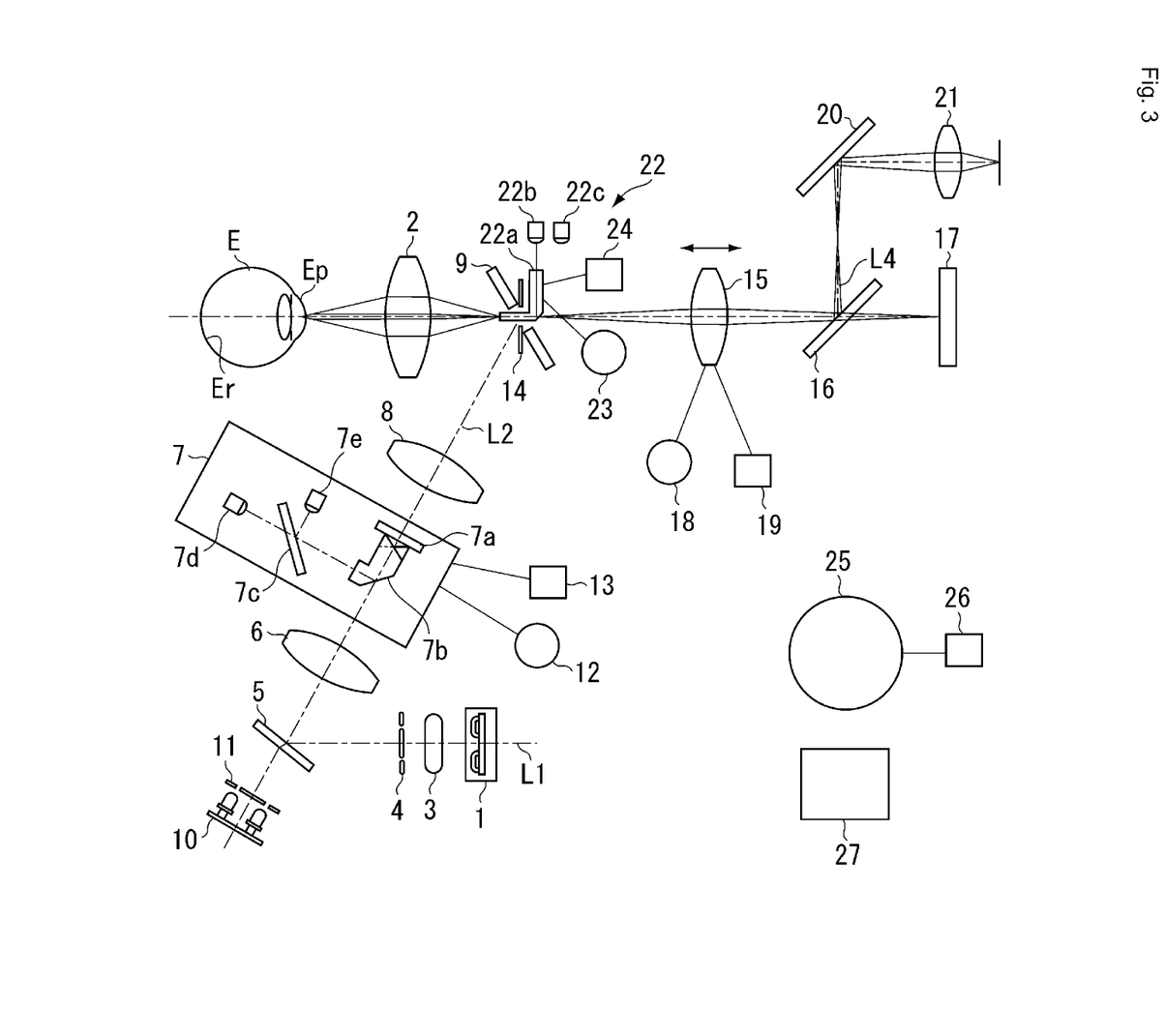
FIG. 3 illustrates an optical path diagram when an alignment index is projected by visible light.

FIG. 3 illustrates an optical path diagram when an alignment index is projected by visible light using the visible LED 22b. Visible light entered from the incident portion of the light guide 22a as an index projection unit travels inside in a straight line and a luminous flux reflected on the reflection surface changes an angle to travel in a straight line. Thus, a luminescent spot is formed at an outgoing portion. The luminescent spot formed therein is formed slightly inside an anterior eye portion Ep of the eye to be examined E by the objective lens 2. An alignment index image including the luminescent spot is combined with an ocular fundus image and observed via the finder eyepiece lens 21 in the case of mydriatic observation, namely observation by visible light. At this time, when the luminescent spot of the alignment index is present on both sides of the ocular fundus image by observation, it is indicated that the optical axes of the fundus camera and the eye to be examined E are aligned. When the luminescent spot is distinctly displayed without blurring, it is indicated that an operation distance between the fundus camera and the eye to be examined E is matched.

Figure 4:
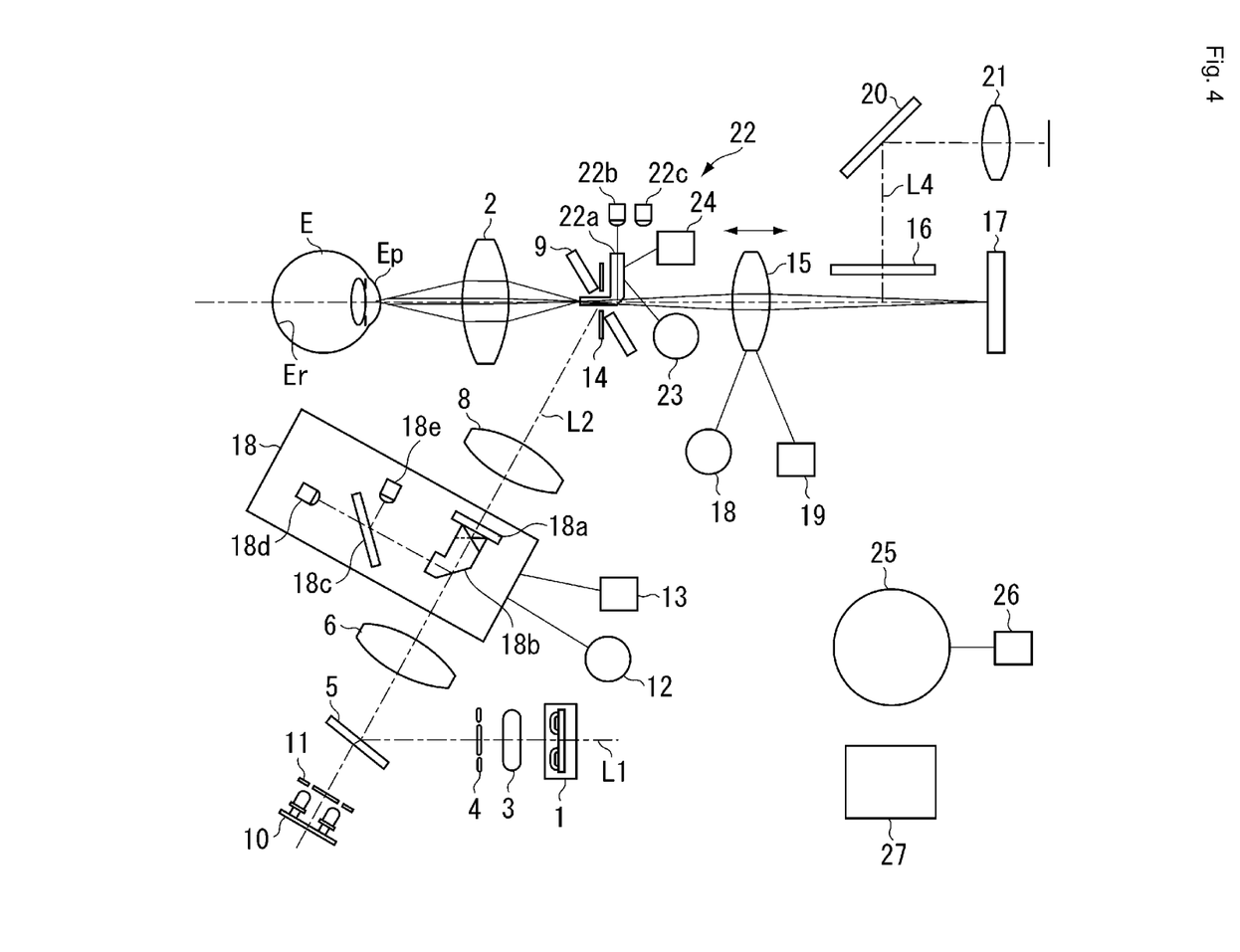
FIG. 4 illustrates an optical path diagram when a light source is changed from visible light to infrared light without adjusting a position of an alignment index.

FIG. 4 illustrates an optical path diagram when the observation light source is changed from visible light of the halogen lamp 1 to infrared light of the infrared LED 10 without adjusting the position of the luminescent spot of the alignment index. In a state of observation by infrared light, the movable mirror 16 is pulled upward and the optical path is changed on the image sensor 17 side. When the visible LED 22b having a long wavelength is used, the length of the optical path is lengthened and an index position to be finally formed is deviated backward more than that of the image sensor 17. Therefore, if the position of the luminescent spot of the alignment index is not adjusted, an operation distance cannot correctly be matched.

Figure 5:
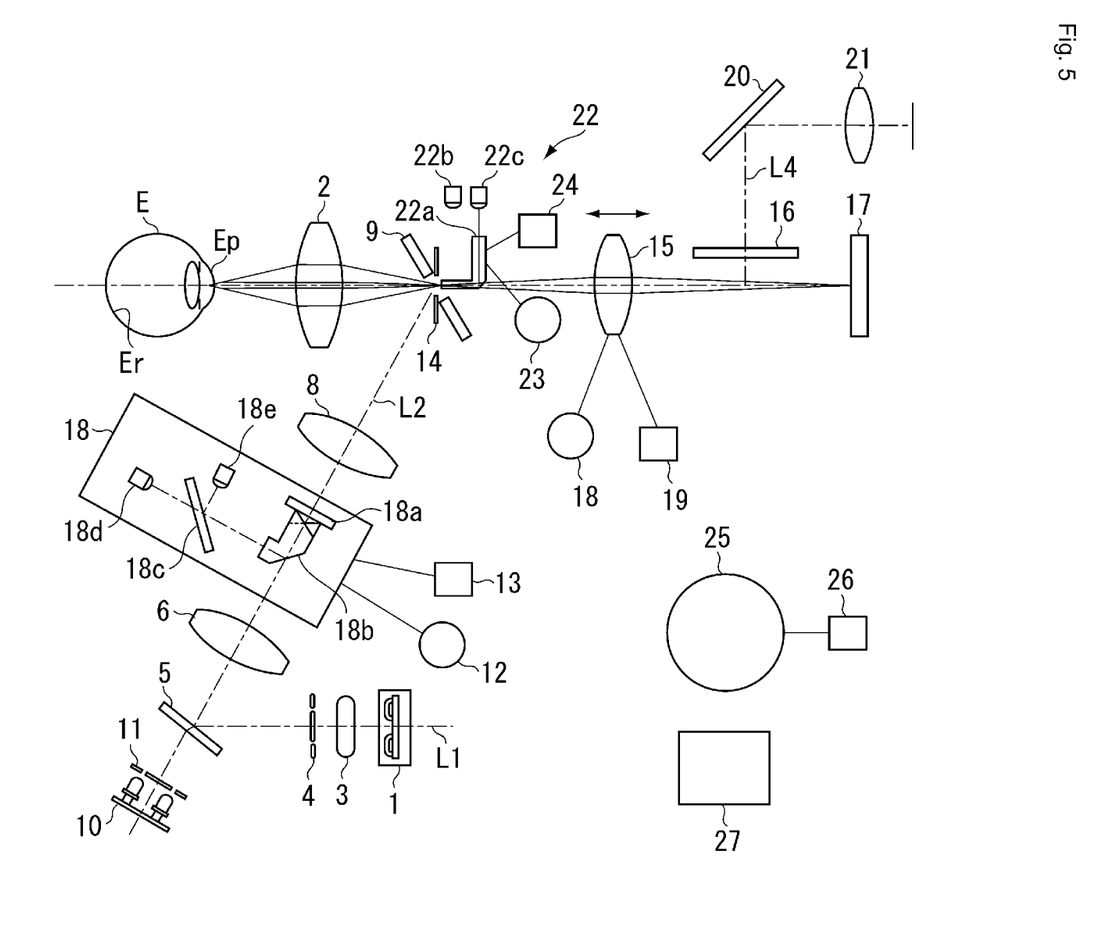
FIG. 5 illustrates an optical path diagram when a light source is changed from visible light to infrared light by adjusting a position of an alignment index.

FIG. 5 illustrates an optical path diagram when the light source is changed from the visible LED 22b to the infrared LED 22c by adjusting the position of the alignment index in the case as described above. The light guide 22a is shifted by the alignment index drive motor 23 so that the incident portion faces the infrared LED 22c. At this time, the outgoing portion of the light guide 22a is set in a position on which an image is formed on the image sensor 17 when the operation distance is appropriate on the wavelength of the infrared LED 22c. In other words, the visible LED 22b and the infrared LED 22c are disposed side by side in the direction of the optical axis and an interval thereof corresponds to a distance that each light can form an image on the image sensor 17 when the operation distance is appropriate. By employing such the configuration, when the light guide 22a is shifted, the facing LED is changed. Thus, while changing a luminescent color, a position of a luminescent point, namely the luminescent spot of the alignment index can also be changed.

Figure 6:
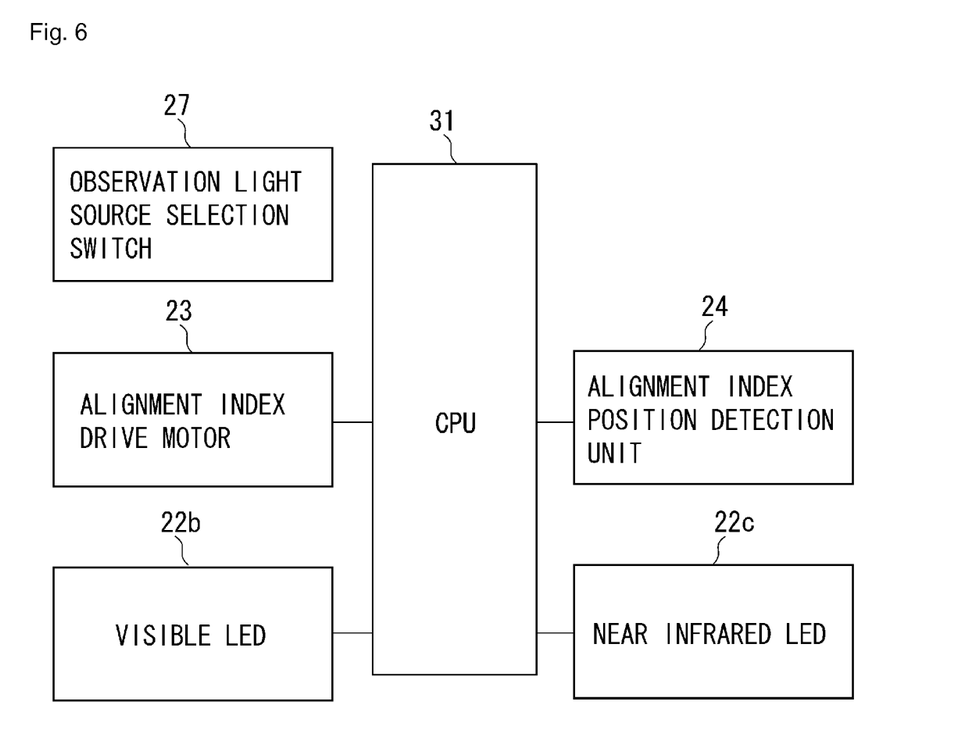
FIG. 6 illustrates a block circuit diagram.

FIG. 6 illustrates a block circuit diagram. The entire operation of the fundus camera is controlled by a central processing unit (CPU) 31. The observation light source selection switch 27 selects observation by infrared light and observation by visible light corresponding to an observation mode to be desired by a subject. In the present exemplary embodiment, the observation light source is directly selected by the observation light source selection switch 27. However, if a photographing mode is selected from non-mydriatic/mydriatic photographing, infrared light/visible light is selected by the observation light source in conjunction therewith.

The alignment index drive motor 23 and the alignment index position detection unit 24 are connected to the CPU 31, so that the alignment index can be shifted to a desired position and the position can be detected. A change between the visible LED 22b and the infrared LED 22c is also controlled by the CPU 31, and the visible LED 22b and the infrared LED 22c can be turned ON and OFF at a desired time.

Figure 7:
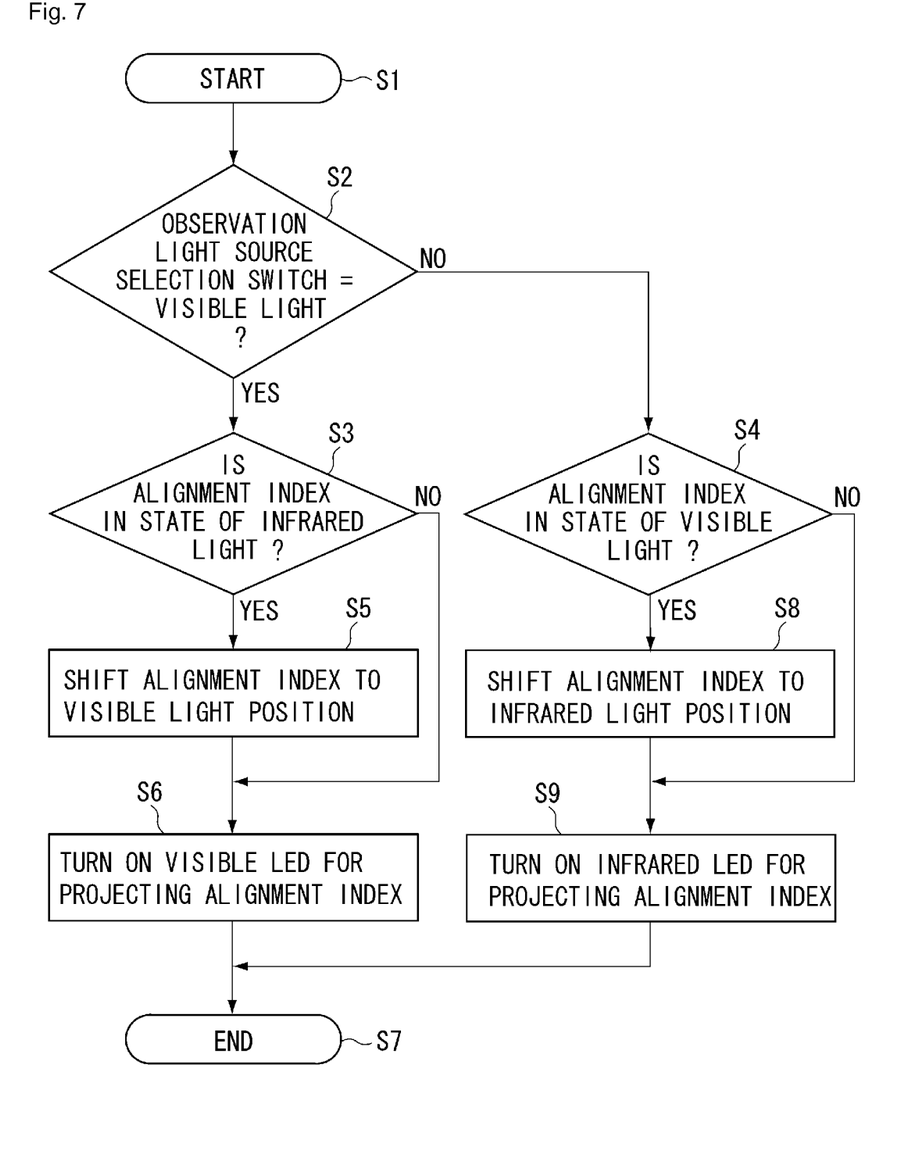
FIG. 7 is a flowchart illustrating an operation for changing a color and a position of an alignment index.

FIG. 7 is a flowchart illustrating an operation executed by the CPU 31 for changing a color and a position of an alignment index. In step S1, the operation is started. In step S2, a state of the observation light source selection switch 27 is checked. If visible light is selected (YES in step S2), the processing proceeds to step S3. If infrared light is selected (NO in step S2), the processing proceeds to step S4.

In step S3, a state of an alignment index is checked by the alignment index position detection unit 24. When it is in the state of infrared light (YES in step S3), the processing proceeds to step S5. When it is in the state of visible light (NO in step S3), the processing proceeds to step S6. In step S5, the light guide 22a is shifted by the alignment index drive motor 23, and the position of the alignment index is shifted to the visible LED 22b. In step S6, the visible LED 22b for projecting the alignment index is turned on. In step S7, a series of sequences ends.

In step S4, the state of the alignment index is checked by the alignment index position detection unit 24. When it is in the state of visible light (YES in step S4), the processing proceeds to step S8. When it is in the state of infrared light (NO in step S4), the processing proceeds to step S9. In step S8, the light guide 22a is shifted by the alignment index drive motor 23, and the position of the alignment index is shifted to the infrared LED 22c. In step S9, the infrared LED 22c for projecting the alignment index is turned on. In step S7, a series of sequences ends.

In the present exemplary embodiment, the alignment index is generated using the light guide 22a. If an optical fiber or other light-guiding members is used, a similar effect can be obtained.

Figure 8:
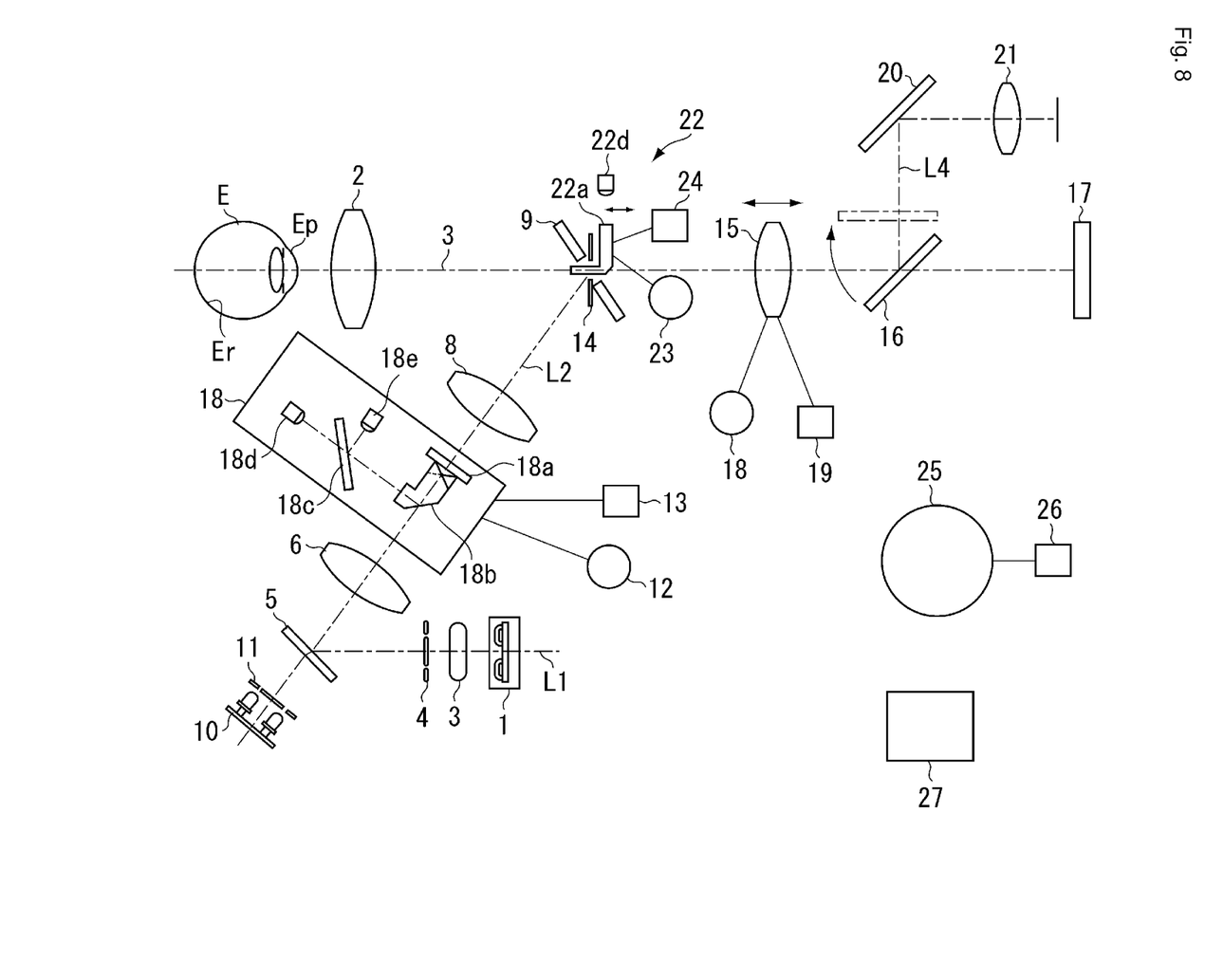
FIG. 8 illustrates a block diagram according to a second exemplary embodiment.

FIG. 8 illustrates a block diagram of a fundus camera according to a second exemplary embodiment. The same reference numeral as that in FIG. 1 in the first exemplary embodiment indicates the same member.

Instead of the visible LED 22b and the infrared LED 22c of the alignment index unit 22, a two-color LED 22d is disposed which is integrated with the light guide 22a and shifted.

This configuration allows the two-color LED 22d to selectively emit light having two different wavelengths. Thus, a change in positions between the visible LED 22b and the infrared LED 22c becomes unnecessary. An optical path length due to a difference in colors can be adjusted by shifting the two-color LED 22d and the light guide 22a.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-124348 filed May 22, 2009, which is hereby incorporated by reference herein in its entirety.

The invention claimed is:

1. An ocular fundus observation apparatus comprising:
   an illumination optical system configured to illuminate an ocular fundus of an eye to be examined;
   an observation photographing optical system configured to observe and photograph the ocular fundus illuminated by the illumination optical system;
   an alignment index unit which is configured to project an alignment index on an anterior eye portion of the eye to be examined in order to adjust a position relation between the observation photographing optical system and the eye to be examined, and is disposed to cause an image of a luminescent spot of the alignment index to be formed when an alignment is aligned with the anterior eye portion by shifting the observation photographing optical system;
   an infrared index light source configured to emit near infrared light and a visible index light source configured to emit visible light which are provided on the alignment index unit;
   an index light source change unit configured to change these index light sources;
   an index projection unit configured to cause the index light source to emit light; and
   a shift control unit configured to control a position of the index projection unit in a direction of an optical axis,
   wherein a position of the luminescent spot of the index projection unit is changed by the shift control unit according to selection of the index light source of the index light source change unit.

2. The ocular fundus observation apparatus according to claim 1, further comprising an observation light source selection unit which can select an observation light source from near infrared light and visible light,
   wherein the index light source change unit operates in conjunction with the observation light source selection unit.

3. The ocular fundus observation apparatus according to claim 1, wherein the index projection unit uses a light guide.

4. The ocular fundus observation apparatus according to claim 1, wherein the index projection unit uses an optical fiber.

5. The ocular fundus observation apparatus according to claim 1,
   wherein an incident portion of the index projection unit is directed in a direction orthogonal to the optical axis, the infrared index light source and the visible index light source are disposed side by side in a direction of the optical axis, and the index projection unit is shifted on either side of the index light sources by the shift control unit.

6. The ocular fundus observation apparatus according to claim 1,
   wherein the infrared index light source is an infrared LED,
   wherein the visible index light source is a visible LED, and
   wherein the alignment index indicates a position relation between the observation photographing optical system and the anterior eye portion of the eye to be examined in a direction of an optical axis of the observation photographing optical system.

7. The ocular fundus observation apparatus according to claim 1, further comprising:
   a selection unit configured to select one of modes including a non-mydriatic mode in which the eye to be examined is to be observed with infrared light and a mydriatic mode in which the eye to be examined is to be observed with visible light,
   wherein the infrared index light source is configured to emit near infrared light in a case where the non-mydriatic mode is selected, and
   wherein the visible index light source is configured to emit visible light in a case where the mydriatic mode is selected.

8. The ocular fundus observation apparatus according to claim 1, further comprising:
   a perforated mirror disposed in the observation photographing optical system,
   wherein the index projection unit is configured to cause the index light source to emit light through a hole of the perforated mirror.

9. The ocular fundus observation apparatus according to claim 8, wherein a shift control unit is configured to control the position of the index projection unit in the direction of the optical axis according to change of the index light sources by the index light source change unit so that an emitting portion of the index projection unit disposed in the hole is moved in a direction of the optical axis of the observation photographing optical system.

10. An ocular fundus observation method comprising:
    projecting an alignment index on an anterior eye portion of an eye to be examined in order to observe an ocular fundus of the eye to be examined illuminated by an illumination optical system and to adjust a position relation between an observation photographing optical system for photographing and the eye to be examined; and
    controlling a position of a projection optical unit configured to project light emitted by a selected index light source to the anterior eye portion in a direction of an optical axis according to selection of either an infrared index light source configured to emit near infrared light or a visible index light source configured to emit visible light.

11. The ocular fundus observation method according to claim 10, further comprising:
    selecting one of modes including a non-mydriatic mode in which the eye to be examined is to be observed with infrared light and a mydriatic mode in which the eye to be examined is to be observed with visible light; and
    emitting near infrared light from the infrared index light source in a case where the non-mydriatic mode is selected, and emitting visible light from the visible index light source in a case where the mydriatic mode is selected.

12. A non-transitory computer readable storage medium having computer-executable instructions stored thereon for performing the ocular fundus observation method according to claim 10.

13. An ophthalmologic apparatus comprising:
a photographing optical system configured to image light returning from an eye to be examined illuminated via an illumination optical system on an imaging unit;
a selection unit configured to select a wavelength of alignment index light indicating a position relation between the photographing optical system and the eye to be examined in a direction of an optical axis the photographing optical system; and
an index projection unit configured to project alignment index light having the selected wavelength to the eye to be examined,
wherein the photographing optical system is configured such that a difference in optical path length corresponding to a difference in wavelength of the alignment index light projected to the eye to be examined by the index projection unit is to be adjusted.

14. The ophthalmologic apparatus according to claim 13, further comprising:
a moving unit configured to move the index projection unit along the optical axis of the photographing optical system; and
a control unit configured to control the moving unit so that the difference in optical path length is adjusted according to selection by the selection unit.

15. The ophthalmologic apparatus according to claim 14, wherein the control unit is configured to control the moving unit to move the index projection unit to a position on the optical path of the photographing optical system corresponding to the selected wavelength.

16. An ophthalmologic apparatus comprising:
a photographing optical system configured to image light returning from an eye to be examined illuminated via an illumination optical system on an imaging unit;
a selection unit configured to select a wavelength of alignment index light indicating a position relation between the photographing optical system and the eye to be examined in a direction of an optical axis the photographing optical system;
an index projection unit configured to project alignment index light having the selected wavelength to the eye to be examined; and
a control unit configured to control the moving unit to move the index projection unit to a position on the optical path of the photographing optical system corresponding to the selected wavelength according to selection by the selection unit.

17. The ophthalmologic apparatus according to claim 16, wherein the selection unit is configured to select one of modes including a non-mydriatic mode in which the eye to be examined is to be observed with infrared light and a mydriatic mode in which the eye to be examined is to be observed with visible light,
wherein the index projection unit is configured to project infrared alignment index light to the eye to be examined in a case where the non-mydriatic mode is selected, and
wherein the index projection unit is configured to project visible alignment index light to the eye to be examined in a case where the mydriatic mode is selected.

18. The ophthalmologic apparatus according to claim 17, further comprising:
an infrared LED configured to emit the infrared alignment index light; and
a visible LED configured to emit the visible alignment index light.

19. The ophthalmologic apparatus according to claim 16, further comprising:
a perforated mirror disposed in the photographing optical system,
wherein the index projection unit is configured to project the alignment index light having the selected wavelength to the eye to be examined through a hole of the perforated mirror.

20. The ophthalmologic apparatus according to claim 19, further comprising:
a moving unit configured to move an emitting portion of the index projection unit disposed in the hole in the direction of the optical axis of the photographing optical system,
wherein the control unit is configured to control the moving unit according to the selection by the selection unit.

21. The ophthalmologic apparatus according to claim 16, wherein the selection unit is configured to select a wavelength of illumination light to illuminate the eye to be examined via the illumination optical system, and
wherein the index projection unit is configured to project alignment index light having a wavelength corresponding to the selected wavelength to the eye to be examined according to selection by the selection unit.

22. An ophthalmologic method comprising:
selecting a wavelength of alignment index light indicating a position relation between a photographing optical system and an eye to be examined in a direction of an optical axis of the photographing optical system, the photographing optical system configured to image light returning from the eye to be examined illuminated via an illumination optical system on an imaging unit; and
moving an index projection unit configured to project alignment index light having the selected wavelength to the eye to be examined to a position on the optical axis of the photographing optical system corresponding to the selected wavelength according to selection in the selecting.

23. The ophthalmologic method according to claim 22, wherein one of modes including a non-mydriatic mode in which the eye to be examined is to be observed with infrared light and a mydriatic mode in which the eye to be examined is to be observed with visible light is selected in the selecting,
wherein infrared alignment index light is projected by the index projection unit to the eye to be examined in a case where the non-mydriatic mode is selected, and
wherein visible alignment index light is projected by the index projection unit to the eye to be examined in a case where the mydriatic mode is selected.

24. A non-transitory computer readable storage medium having computer-executable instructions stored thereon for performing the ophthalmologic method according to claim 22.

* * * * *